United States Patent

Hiejima et al.

[11] Patent Number: 5,931,193
[45] Date of Patent: Aug. 3, 1999

[54] FLOW RATE CONTROL DEVICE HAVING PRIMING MECHANISM

[75] Inventors: Katsuhiro Hiejima, Ohtsu; Takeshi Mori, Ibaragi, both of Japan

[73] Assignee: Nissho Corporation, Osaka, Japan

[21] Appl. No.: 08/862,436

[22] Filed: May 23, 1997

[30] Foreign Application Priority Data

May 23, 1996 [JP] Japan .................................. 8-128067

[51] Int. Cl.$^6$ ...................................................... A61M 5/14
[52] U.S. Cl. ........................... 137/599; 417/478; 604/247
[58] Field of Search ................................ 137/599, 599.1; 417/478; 604/133, 153, 247

[56] References Cited

U.S. PATENT DOCUMENTS

| | | | |
|---|---|---|---|
| 1,352,306 | 9/1920 | Mott | 417/478 |
| 3,739,794 | 6/1973 | Lindgren | 137/599.1 X |
| 4,245,636 | 1/1981 | Sparks et al. | 128/214 |
| 4,741,733 | 5/1988 | Winchell . | |
| 4,904,239 | 2/1990 | Winchell et al. . | |
| 5,316,452 | 5/1994 | Bogen et al. | 417/478 X |
| 5,556,258 | 9/1996 | Lange et al. | 417/478 X |

FOREIGN PATENT DOCUMENTS

| | | |
|---|---|---|
| 0 067 458 A2 | 12/1982 | European Pat. Off. . |
| 2.112.208 | 6/1972 | France . |
| 05237194 | 9/1993 | Japan . |
| 2 054 802 | 2/1981 | United Kingdom . |
| WO 95/08359 | 3/1995 | WIPO . |

*Primary Examiner*—Stephen M. Hepperle
*Attorney, Agent, or Firm*—Kubovcik & Kubovcik

[57] ABSTRACT

A flow rate control device which does not constitute an obstruction when it is connected to a liquid medicine continuous injector, which is not influenced by the body temperature of a patient and which can perform a priming operation of the liquid medicine continuous injector in a short period of time is disclosed. The control device is provided with a reservoir, a flow rate control tube and a release valve, which are preferably incorporated in a housing. The housing is provided with a through hole such that the reservoir can be pressed by a pressing means, and is also provided with a liquid medicine inlet and a liquid medicine outlet for the reservoir. A check valve is preferably provided in the liquid medicine inlet and the flow rate control tube and the release valve are provided in the liquid medicine outlet. The flow rate control tube and the release valve are provided coaxially with each other or in parallel with each other.

5 Claims, 4 Drawing Sheets

FLOW RATE CONTROL DEVICE HAVING PRIMING MECHANISM

BACKGROUND OF THE INVENTION

1. Field of the Invention

The present invention relates to a flow rate control device having a priming mechanism. More particularly, the present invention relates to a flow rate control device capable of instantaneously priming a tube on the downstream side of the device by pressing a reservoir encased therein. The flow rate control device of the present invention is particularly suitable for use with a ballooned liquid medicine continuous injector. Such an injector is used as a means for administering an analgesic, an anesthetic, an antibiotic, a carcinostatic agent into blood vessels, and the like continuously and in a small amount by injecting liquid medicine filled in a balloon made of an elastomeric material by the contracting force of the balloon.

2. Description of Related Art

In recent years a ballooned medicine continuous injector has been used as a means of administering an analgesic, an anesthetic, an antibiotic, a carcinostatic agent into blood vessels, and hypodermic portions and epidural portions or the like continuously and in a small amount (Japanese Examined Patent Publication No. JP-A-62-501333, Japanese Unexamined Patent Publication No. JP-A-5-237194 and the like). To use the injector, it is necessary to first fill the liquid medicine in a tube and prime the tube to vent the inside air before injecting the liquid medicine into a patient.

In the liquid medicine continuous injector of Japanese Examined Patent Publication No. JP-A-62-501333, a flow rate control tube is provided adjacent to a tubular connecting piece on the side of a patient and, therefore, the priming operation does not require a lot of time. However, the injector has the drawbacks that it creates an obstruction because the portion thereof adjacent to the patient is large, flow rate is varied by the influence of the body temperature of the patient, and the like. The liquid medicine continuous injector of Japanese Unexamined Patent Publication No. JP-A-5-237194 does not cause the above-described problems since the flow rate control tube is provided at a position remote by at least 30 cm or more from a connecting end disposed on the downstream side of the tube. However, it has the drawback that a lot of time is required for priming a tube downstream from the flow rate control tube since the tube is constituted by a tube having a very small inner diameter.

SUMMARY OF THE INVENTION

The present invention has been developed in view of the above-described background and it is an object of the present invention to provide a flow rate control device which is not obstructive when connected to a liquid medicine continuous injector, which is not influenced by the body temperature of a patient and which can perform the priming operation of the liquid medicine continuous injector in a short period of time.

A construction providing a priming mechanism to a flow rate control tube is adopted in the present invention as a flow rate control device in order to resolve the above-described problems.

According to the present invention a flow rate control device is provided having a priming mechanism comprising a press-deformable reservoir having a liquid medicine inlet and a liquid medicine outlet, a release valve provided at the liquid medicine outlet side of the reservoir and capable of allowing a liquid medicine in the reservoir to flow out when opened under a constant pressure, and a flow rate control tube for controlling the flow rate of the liquid medicine flowing out of the reservoir by the flow resistance thereof. The flow rate control tube can be provided coaxially with the release valve or in parallel with the release valve. Also, it is preferable that a check valve for preventing a back flow of the liquid medicine out of the reservoir is provided in the liquid medicine inlet. The reservoir may be incorporated into a housing which forms the liquid medicine inlet and the liquid medicine outlet of the reservoir and, in this case, a through hole capable of having a reservoir pressing means inserted therein is provided in the housing.

DETAILED DESCRIPTION FOR THE PREFERRED EMBODIMENTS

The following is an explanation of embodiments of the present invention with reference to the drawings.

Figure 1:
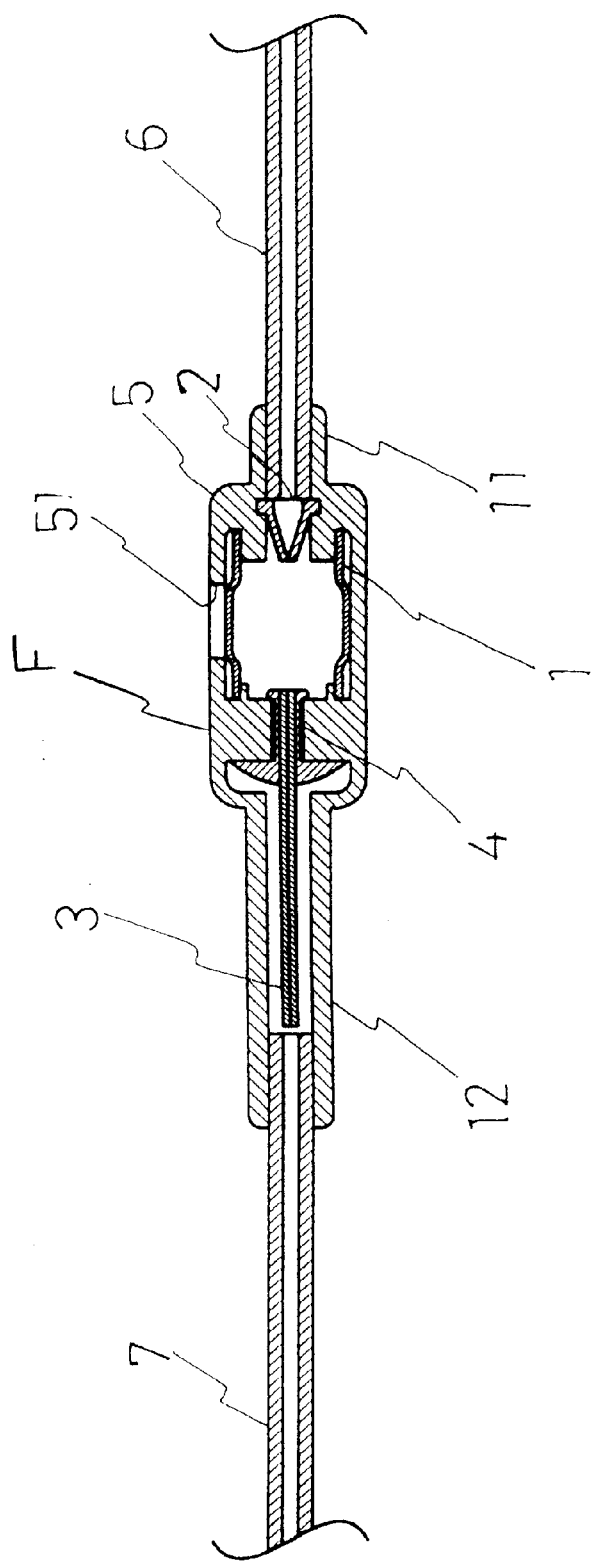
FIG. 1 is a longitudinal sectional view showing an embodiment of the flow rate control device of the present invention.
Figure 2:
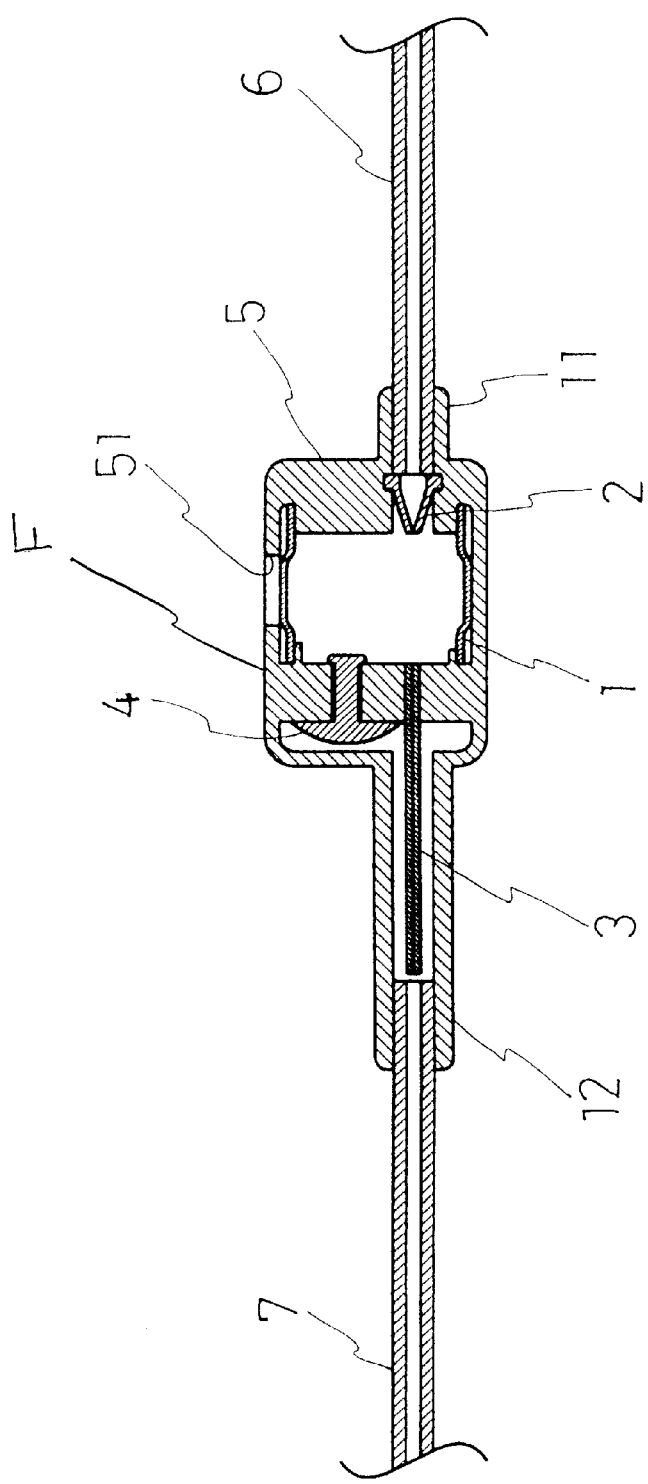
FIG. 2 is a longitudinal sectional view showing another embodiment of the flow rate control device of the present invention.

As shown in FIGS. 1 and 2, a flow rate control device F is provided with a reservoir 1, a flow rate control tube 3 and a release valve 4. The reservoir 1, the flow rate control tube 3 and the release valve 4 are preferably incorporated in a housing 5. According to FIG. 1, the flow rate control tube 3 and the release valve 4 are coaxially arranged, and according to FIG. 2, the flow rate control tube 3 and the release valve 4 are arranged in parallel with each other. A through hole 51 is provided in the housing 5 such that the reservoir 1 can be pressed, or squeezed, by a pressing means (not shown). A liquid medicine inlet 11 and the liquid medicine outlet 12 for the reservoir 1 are provided in the housing 5. A check valve 2 is preferably provided in the liquid medicine inlet 11 and the flow rate control tube 3 and the release valve 4 are arranged in the liquid medicine outlet 12.

The reservoir 1 is typically a press-deformable bag composed of a flexible resin such as polyethylene, polypropylene, polyester or the like, or an elastic rubber material such as polyisoprene, silicone rubber or the like, which is provided with the liquid medicine inlet 11 and the liquid medicine outlet 12. The reservoir 1 can be incorporated in the housing 5. In this case, the liquid medicine inlet 11 and the liquid medicine outlet 12 are integrally formed in the housing 5 having a through hole 51. The through hole 51 is provided to enable pressing to deform the reservoir 1 by means of a pressing means (not shown) inserted therein. The liquid medicine inlet 11 and the liquid medicine outlet 12 are respectively connected with connection tubes 6 and 7 as shown in FIGS. 1 and 2. The liquid medicine inlet 11 is preferably provided with a check valve 2 for preventing liquid medicine from flowing back into the upstream connection tube 6 and the flow rate control tube 3 and the release valve 4 are provided in the liquid medicine outlet 12. Although the flow rate control tube 3 and the release valve 4 are preferably coaxially installed to make the overall device compact as shown in FIG. 1, as illustrated in FIG. 2, they can be provided in parallel with each other.

Incidentally, although the reservoir 1 can be depressed by inserting a finger or the like into the through hole 51 of the housing 5, it is preferable to use an exclusively-used pressing piece (not illustrated) such that a patient can not press the reservoir 1 at his or her own discretion and it is particularly preferable that the through hole 51 is undetachably closed simultaneously with the priming operation.

The flow rate control tube 3 is constituted by a tube having an extremely small diameter such that the flow rate of liquid medicine flowing out of the reservoir 1 is controlled by the flow resistance of the tube. The tube 3 is generally composed of a synthetic resin such as a polyolefin, polyvinyl chloride, polyester, polyamide, polyurethane, polyacrylate, polymethacrylate, polycarbonate or the like. In respect of the dimensions of the flow rate control tube 3, the inner diameter is preferably 10 to 500 $\mu$, and more preferably 50 to 300 $\mu$; the length is preferably 1 cm or more and the outer diameter is preferably 5 to 500 times larger than the inner diameter. When the inner diameter of the flow rate control tube 3 is less than 10 $\mu$, air in the liquid medicine tends to adhere onto the inner wall of the tube whereby the flow of liquid medicine is stopped. When the inner diameter exceeds 500 $\mu$, the control of the flow rate of the liquid medicine tends to become difficult.

The release valve 4 is a valve for allowing the liquid medicine to flow out of the reservoir 1 when the valve is opened by a certain pressure. The valve is normally closed and is opened when the inner pressure of the reservoir 1 becomes larger than a predetermined value. As such a release valve, a parasol type valve or a duck bill type valve is generally adopted. However, if the flow rate control tube 3 (as illustrated in FIG. 1) is installed coaxially with the release valve 4, the parasol type valve is used.

The following is an explanation of the priming operation of the flow rate control device F of the present invention.

Figure 4:
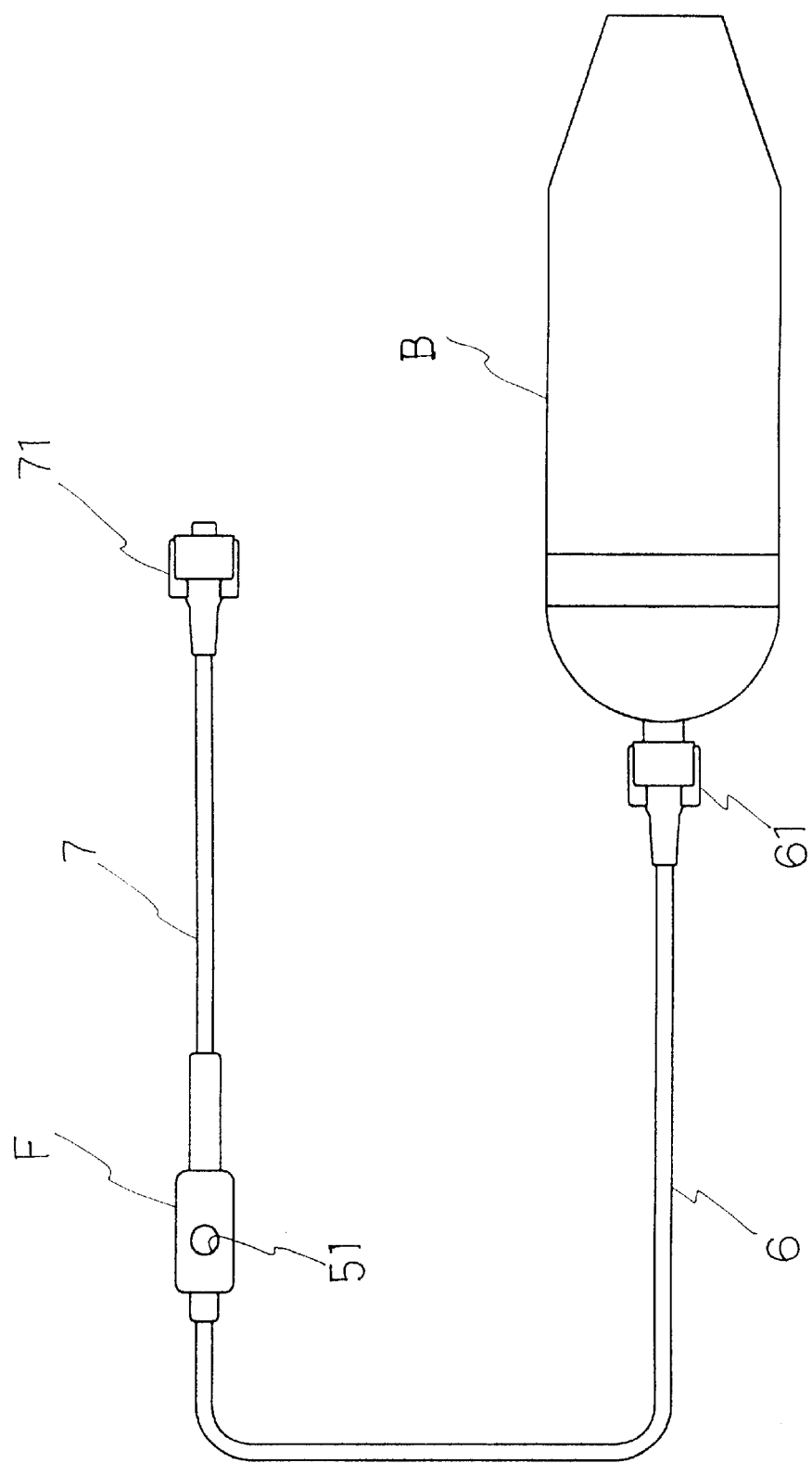
FIG. 4 is a view showing a state where the flow rate control device illustrated in FIG. 1 is connected to a ballooned liquid medicine continuous injector.

As shown in FIG. 4, the flow rate control device F is used by connecting a connector 61 at a distal end of connection tube 6 to a liquid medicine continuous injector B. Although a time period of several minutes is required in priming a portion downstream from the flow rate control device F according to a conventional flow rate control device, the priming operation can be conducted instantaneously by adopting the flow rate control device F of the present invention. Incidentally, numeral 71 in FIG. 4 designates a connector for a connection to a catheter.

Figure 3:
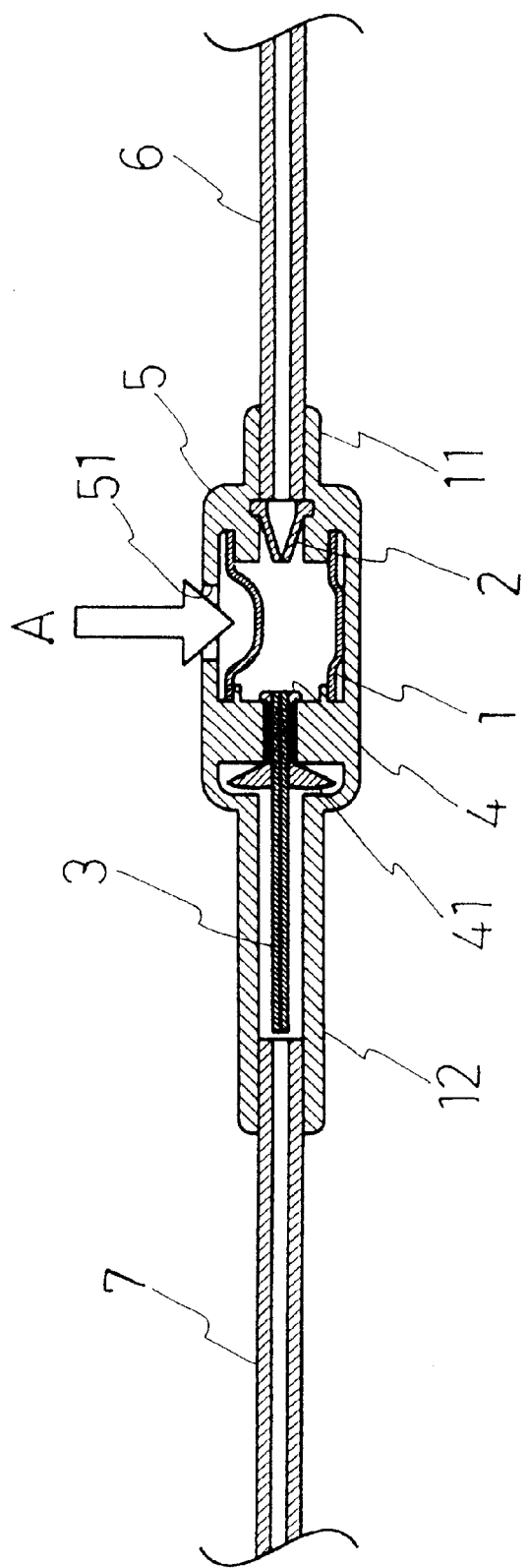
FIG. 3 is an explanatory view for explaining the priming operation of the flow rate control device illustrated in FIG. 1.

As illustrated in FIG. 3, the reservoir 1 may be pressed by inserting an exclusively-used pressing piece in the direction of the arrow A to perform the priming operation. When the reservoir 1 is pressed, the inner pressure is increased whereby valve 41 of the release valve 4 is opened and the liquid medicine in the reservoir 1 is discharged in one stroke around the release valve 4 and into the connection tube 7 to prime the connection tube 7 and a medicine liquid passage downstream from the connection tube 7.

After finishing the priming operation, liquid medicine in reservoir 1 flows through the flow rate control tube 3 and is injected into the body of a patient in a very small amount.

As is apparent from the above-described explanation, the following effects can be achieved by adopting the flow rate control device of the present invention: (1) the device is not obstructive when it is connected to a liquid medicine continuous injector, (2) liquid medicine can be injected accurately since the device is not influenced by the body temperature of a patient, (3) the priming operation of a liquid medicine continuous injector can be carried out in a short period of time, and the like.

What is claimed is:

1. A flow rate control device having a priming mechanism, said device comprising;

a press-deformable reservoir having a liquid medicine inlet and a liquid medicine outlet;

a release valve provided in the liquid medicine outlet of the reservoir and which permits a liquid medicine to flow out of the reservoir when the release valve is caused to open by pressure applied to the reservoir; and a flow rate control tube for controlling a flow rate of the liquid medicine out of the reservoir by flow resistance of the tube and which is directly fluid-communicated with said reservoir.

2. The flow rate control device according to claim 1, wherein the flow rate control tube is provided coaxially with the release valve.

3. The flow rate control device according to claim 1, wherein the flow rate control tube is provided in parallel with the release valve.

4. The flow rate control device according to any one of claims 1 through 3, wherein a check valve for preventing the liquid medicine from flowing back out of the reservoir is installed at the liquid medicine inlet.

5. The flow rate control device according to any one of claims 1 through 3, wherein the reservoir is incorporated in a housing having the liquid medicine inlet and the liquid medicine outlet of the reservoir and which is provided with a through hole capable of receiving a means for pressing the reservoir.

* * * * *